United States Patent [19]

Barken

[11] Patent Number: 5,377,683
[45] Date of Patent: Jan. 3, 1995

[54] ULTRASOUND-LASER SURGERY APPARATUS AND METHOD

[76] Inventor: Israel Barken, 6823 Deer Hollow Pl., San Diego, Calif. 92120

[21] Appl. No.: 741,198

[22] Filed: Jul. 30, 1991

Related U.S. Application Data

[63] Continuation of Ser. No. 387,949, Jul. 31, 1989, abandoned.

[51] Int. Cl.⁶ .......................... A61B 8/12; A61B 17/36
[52] U.S. Cl. ...................... 128/660.03; 606/7; 606/12; 606/15; 606/17
[58] Field of Search .................. 606/7, 12, 14, 15, 17, 606/18; 128/397, 398, 660.03, 662.06; 607/89

[56] References Cited

U.S. PATENT DOCUMENTS

| | | | |
|---|---|---|---|
| 4,445,892 | 5/1984 | Hussei et al. | 606/15 X |
| 4,576,177 | 3/1986 | Webster, Jr. | 128/660.03 |
| 4,587,972 | 5/1986 | Morantte, Jr. | 128/660.03 |
| 4,625,724 | 12/1986 | Suzuki et al. | 128/398 X |
| 4,669,467 | 6/1987 | Willett et al. | 606/15 X |
| 4,672,961 | 6/1987 | Davies | 606/15 X |
| 4,672,963 | 6/1987 | Barken | 606/12 |
| 4,681,104 | 7/1987 | Edelman | 606/15 X |
| 4,790,310 | 12/1988 | Ginsburg | 606/15 |
| 4,854,315 | 8/1989 | Stack et al. | 606/7 |
| 4,887,605 | 12/1989 | Angelsen et al. | 128/660.03 |
| 4,911,170 | 3/1990 | Thomas, III et al. | 128/660.03 |

*Primary Examiner*—Lee S. Cohen
*Attorney, Agent, or Firm*—David G. Rosenbaum

[57] ABSTRACT

A catheter having an ultrasound transducer and associated electrically wiring conducted through a sidewall thereof and a plurality of optical fibers provided in the lumen of the catheter for conveying laser light from an external laser source to the tip of the catheter. The laser irradiation is angularly emitted from the tip of each optical fiber. The ultrasound and the laser are connected to a computer system which is used to display ultrasonic images of internal tissue areas within the patient's body and control firing of the laser in response to delimiting input from the physician.

18 Claims, 2 Drawing Sheets

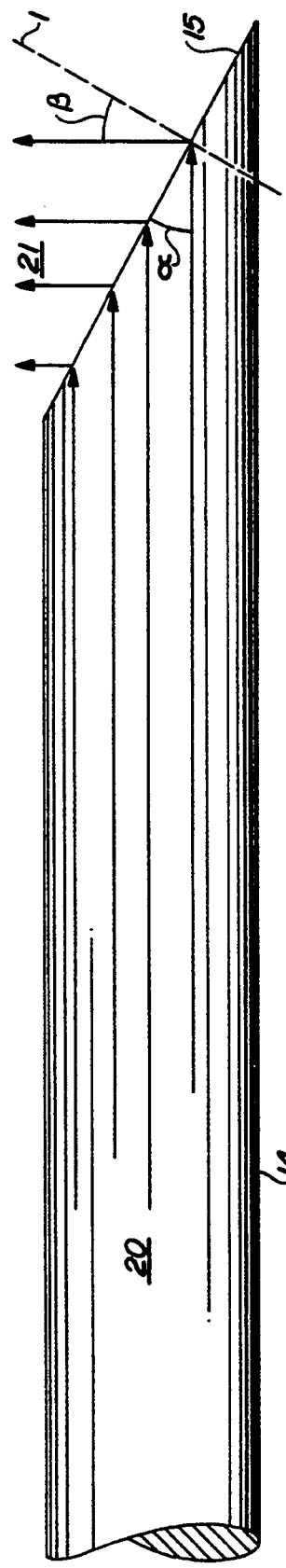
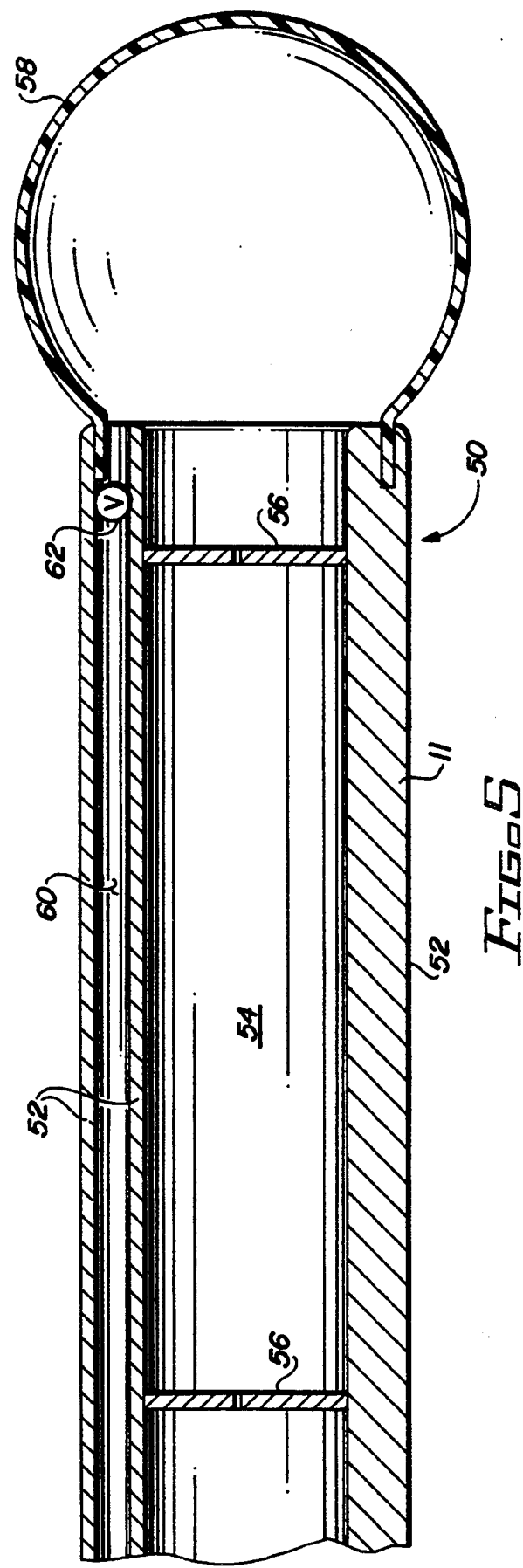

ULTRASOUND-LASER SURGERY APPARATUS AND METHOD

This is a continuation of copending application(s) Ser. No. 07/387,949 filed on Jul. 31, 1989, now abandoned.

BACKGROUND OF THE INVENTION

The present invention relates generally to a computerized ultrasound-laser surgical device and method for imaging internal tissue areas and irradiating selective regions of the tissue area with laser to surgically remove unwanted tissue residing in the imaged tissue area. More specifically, the present invention provides a catheter having an ultrasound transducer and associated electrically wiring conducted through a sidewall thereof and a plurality of optical fibers provided in the lumen of the catheter for conveying laser light from an external laser source to the tip of the catheter. The ultrasound and the laser are connected to a computer system which is used to display ultrasonic images of internal tissue areas within the patient's body which is used to display ultrasonic images of internal tissue areas within the patient's body which convey tissue information to the physician. By interacting with the computer system, the physician is able to selectively irradiate and destroy unwanted tissue from the ultrasonically displayed area by controlling the direction, duration and intensity of the laser burst.

The use of laser radiation to destroy certain types of structures or tissues has become increasingly accepted. Conventional surgical procedures often require radical invasion of healthy body tissue, whereas the known laser surgical techniques permit non-open surgery in which the laser is applied to selected tissue through a light pipe, cystoscope or laser probe. U.S. Pat. No. 4,672,963 (hereinafter the "Barken Patent") issued to Israel Barken, the inventor hereof, on Jun. 16, 1987, which is hereby incorporated by reference thereto, discloses an apparatus and method for computer controlled laser surgery which introduces an ultrasound probe and a laser probe into the body of the patient and destroys unwanted tissue by visualizing the tissue region though ultrasonic imaging and irradiating a selected tissue area to be destroyed. U.S. Pat. No. 4,576,177 (hereinafter the "Webster Patent) issued to Wiltos W. Webster, Jr. on Mar. 18, 1986 discloses a catheter for removing arteriosclerotic plaque. The catheter disclosed in the Webster Patent consists of a single optical fiber for transmitting laser irradiation and an ultrasonic transducer mounted at the tip of the catheter for transmitting and receiving ultrasonic signals.

An important distinction between the Barken Patent and The Webster patent is the Webster Patent utilizes a rather arcane ultrasound transducer/receiver sensitive only to ultrasonic signal echoes which produce an electronic signature, on an oscilloscope, of the tissue character and the blood flow velocity between two selected distances from the catheter tip. In Barken, however, it is taught that an ultrasound probe may be used to display a visual image of the internal tissue area. An important advantage of the Barken system, therefore, is that it eliminates the need for electronic signature interpretation to properly characterize the tissue while permitting the physician to actually visualize the pertinent tissue area. To further facilitate surgical accuracy, Barken teaches the use of a computer system to construct real time three-dimensional images of the tissue area to be irradiated and to store tissue and laser irradiation data and control the intensity and duration of irradiation.

Despite the significant advances in the art provided by the Webster and Barken Patents, directional control of the laser firing with respect to the tissue to be irradiate is problematic. The Webster Patent teaches that is known to mount the optical fiber in the central opening of the ultrasound transducer. In Webster, the ultrasound transducer is angularly mounted on the tip of the catheter. A microlens is mounted within the central opening of the transducer and optically coupled to the optical fiber to change the direction of the laser irradiation to about the center of the transmitted ultrasonic signal. Thus, the catheter of Webster is capable only of unidirectional laser firing and requires physician intervention to redirect the laser. Similar to the Webster catheter, all known laser surgical apparatus permit only single-direction laser firing.

Accordingly, there are several disadvantages associated with the apparatus disclosed in the Webster Patent. Specifically, ultrasonic imaging of the tissue area is not provided thereby requiring the physician to interpret electronic signals rather than images, the single laser fiber permits only single-direction laser firing and requires manual manipulation of the catheter to change the laser firing direction and there is no computer system to store tissue information and control laser firing to preserve healthy tissue and destroy only unwanted tissue. The Barken Patent provides a computer system to process information from the ultrasound and display real-time constructed three-dimensional images on an associated monitor and control laser activation and power, and, therefore, represents a major advancement over the Webster Patent. However, the Barken Patent is silent on any specific apparatus to incorporate both an ultrasound probe to provide real time tissue images and a laser probe which is capable of multi-directional firing without requiring manual manipulation to adjust laser firing direction.

SUMMARY OF THE INVENTION

In accordance with the present invention, there is provided an apparatus for determining the position and character of internal tissue or structures and destroying unwanted tissue or structures within the internal body regions without substantially affecting healthy tissue.

The apparatus consists of a catheter, an ultrasound transmitting and receiving unit and a laser. The catheter comprises a catheter tube having an ultrasonic transducer mounted at the distal tip of the catheter tube as is known in the ultrasound art. The ultrasonic transducer is electrically connected to the transmitting and receiving units by wires disposed in an extending the length of the catheter tube. A plurality of optical fibers for conveying laser light are disposed about the circumference, either inner or outer, of the catheter tube and extend along its entire length and protrude beyond the ultrasonic transducer. Each of the plurality of optical fibers is optically coupled to a laser source and has an angled terminus which angularly redirects the laser irradiation with respect to the longitudinal axis of the optical fiber. Each of the plurality of optical fibers, therefore, is positioned to aim firing at a fixed sector of the ultrasound image. Both the generation of the ultrasound image and the interaction between the physician and the laser are monitored and controlled by a computer system substantially as disclosed and taught in the Barken Patent, incorporated herein.

The catheter is inserted into a body opening, either natural or surgically created, and manually positioned within the body. The ultrasound is activated to display ultrasonic images of the internal tissue area and the position of the catheter is adjusted until the desired position, represented by the ultrasonic image, is achieved. A three-dimensional image of the tissue area or internal structure is created by varying the position of the catheter along a known longitudinal dimension, resolving a series of two-dimensional images along the longitudinal dimension and using the computer system to reconstruct a three-dimensional real time image of the internal tissue area or structure. After resolving the ultrasound image, the catheter may be repositioned along the known longitudinal dimension to irradiate the unwanted tissue or structure by firing only those laser fibers directed to the relevant sector of the ultrasound image.

As disclosed in the Barken Patent, the physician may interact with the computer by a light pen, mouse, pointing device or other means for designating a portion of the displayed ultrasonic image to delimit the unwanted tissue area. The computer system then directs the appropriate laser fiber or set of laser fibers such as to irradiate only the delimited tissue area.

As an example, not to be construed as limiting the present invention, the catheter of the present invention is introduced intra-urethrally until it reaches the most proximal portion of the prostate. The ultrasound is activated to image the intra-prostatic echo pattern and the gland capsule. The ultrasound images are in transverse cuts. Varying the position of the catheter along the longitudinal direction to the most distal portion of the prostatic urethra, a plurality of transverse images are complied by the computer system to construct a three-dimensional image of the prostate. After production of the three-dimensional image, the catheter is repositioned towards the bladder neck. The physician then instructs the computer system, via interaction through a light pen, mouse or other pointing device or through command entries, to delimit the tissue area, on the displayed ultrasonic image, to be irradiated. The computer will then control the firing of each laser fiber in the direction of the corresponding sector of the delimited ultrasound field. The intensity and duration of the laser irradiation will be stored in the computer and correspond to values previously determined by dosimetry experimentation or tissue changes caused by laser radiation.

Those skilled in the art will understand and appreciate that the present invention may be introduced through any natural tubing system, e.g., transrectally, intravessically, intratracheally, intraesophageally, or intrathecally to resolve and destroy unwanted tissue or structures in virtually any internal body system subserved by a natural passageway. However, in cases where no natural passage exists, such as breast tissue, liver, brain or kidney, it is a further object of the present invention to provide an ultrasound-laser catheter introductory balloon catheter.

The introductory balloon catheter consists of a catheter wall defining an internal lumen, a one-way valve disposed in the terminal end of the lumen, a balloon provided at the terminal end of the catheter and an inflating channel provided in the catheter wall communicating with the balloon.

The introductory balloon catheter is introduced through another dilatation catheter, which has been previously inserted in the tissue in a manner similar to the known techniques for introducing a nephrotomy tube into the kidney. Specifically, this technique entails targeting the lesion inside the body by any known imaging modality, e.g., CT Scan, Magnetic Resonance Imaging, Fluoroscopy, Mammography or Ultrasound. Once the lesion is targeted, a needle is introduced through the tissue to provide a channel in the tissue for introduction of the dilatation catheter. Serial dilatation is then performed by introducing a series of increasingly larger diameter catheters over a guide wire inserted into the tissue. In this manner, therefore, the tissue is gradually dilated until a dilatation catheter of sufficient diameter to accommodate the introductory balloon catheter is provided in the tissue.

In a particular preferred embodiment of the present invention, the introductory balloon catheter is disposed in the body and the ultrasound laser catheter is inserted into the introductory balloon catheter.

These an other features and advantages of the present invention will be better understood with reference to the following detailed description of the preferred embodiments with reference to the accompanying figures, in which like reference numerals identify like features.

BRIEF DESCRIPTION OF THE FIGURES

FIG. 4 is a diagrammatic representation of an enlarged section of an optical fiber of the apparatus of the present invention.

FIG. 5 is a side elevational partial cross-sectional view of an introductory balloon catheter in accordance with the present invention.

DETAILED DESCRIPTION OF THE PREFERRED EMBODIMENTS

Figure 1:
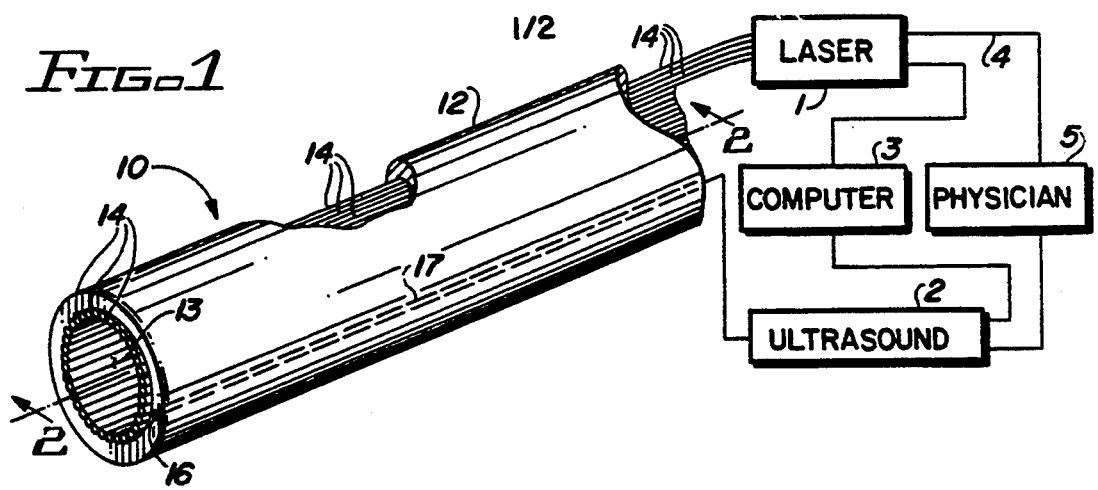
FIG. 1 is a schematic of the apparatus according to the present invention including an enlarged partial cutaway perspective view of a preferred catheter.

The ultrasound laser catheter according to a preferred embodiment of the present invention is illustrated with reference to FIG. 1-3. The ultrasound laser catheter apparatus 10 consists of a laser device 1, an ultrasound device 2 and a catheter 12. Catheter 12 comprises an elongated flexible catheter tube 11 constructed of any suitably biologically and chemically inert material as is well known in the art. The catheter tube 11 has a generally circular, transverse cross section, which defines a lumen 13. The lumen 13 may be use to accommodate a guide wire, introduce fluids, extract fluids or may be closed. The diameter of the catheter tube 11 may vary according to the desired application, i.e., the size of the body tubing system into which it will be introduced.

Figure 2:
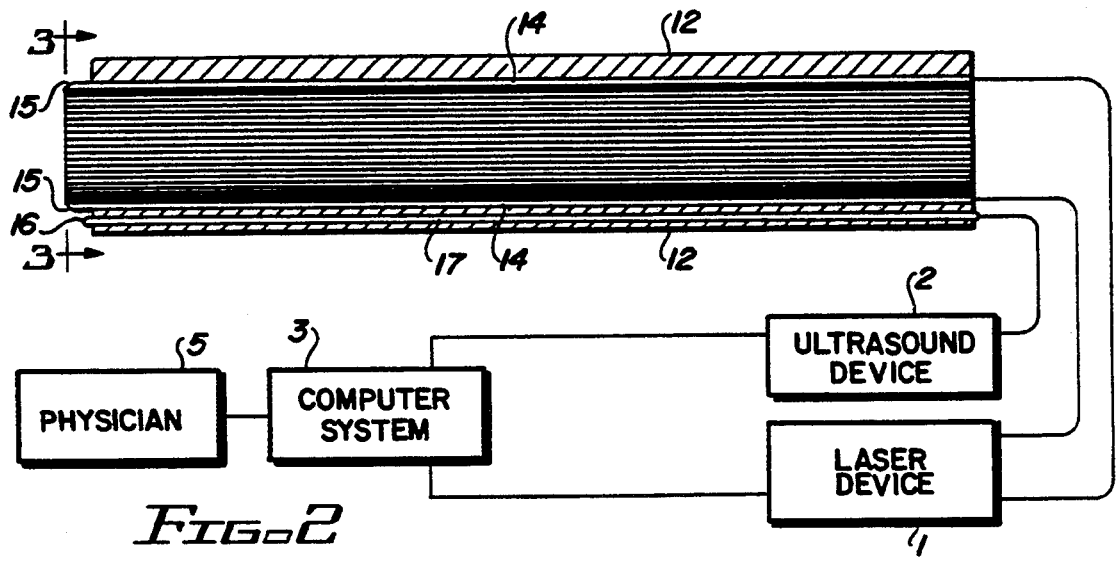
FIG. 2 is a schematic of the apparatus according to the present invention showing a side-elevational cross-sectional view taken along line 2—2 of FIG. 1.
Figure 3:
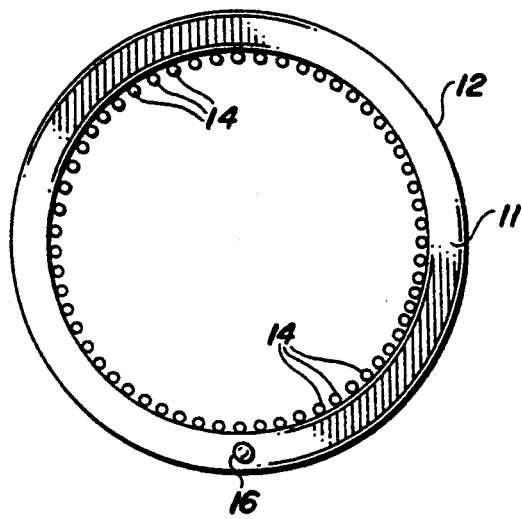
FIG. 3 is an elevational partial cross-sectional view taken along line 3—3 of FIG. 2.

According to one preferred embodiment of the invention, a plurality of optical fibers 14 are disposed about the inner circumference of the lumen 13 as is illustrated in FIGS. 1 and 2. Those skilled in the art will understand and appreciate, however, that according to another preferred embodiment of the invention, the plurality of optical fibers 14 may be disposed about the outer circumference of the catheter tube 12 or within the wall of the catheter tube 12 itself. The optical fibers 14 may be adhered to the catheter tube by any suitable means, i.e., gluing embedding in the material of the catheter tube wall 11.

Each of the plurality of optical fibers 14 are made of a material such as is well known in the optical fiber art and are of sufficient size to transmit sufficient laser irradiation to destroy the internal unwanted tissue or structure without detrimentally increasing thermal conductivity of the optical fiber itself. Each of the plurality of optical fibers 14 protrude from the distal end of the catheter tube 12 and, at the proximal end of the catheter tube 12, are individually connected to and controlled by the laser device 1 and computer system 3.

At least one ultrasonic transducer 16 is mounted at the distal end of the catheter tube 12 and electrically connected to the ultrasound device 2 by suitable electrical conductors 17 which are preferably affixed to or embedded in the catheter tube wall 11. According to the preferred embodiments of the present invention, an ultrasonic transducer 16 and ultrasound device 2 capable of displaying a real-time 360° transverse cross-section, as is known in the ultrasound arts, is employed. Thus, as described in the Barken Patent, incorporated herein by reference thereto, the computer 3 displays a reconstructed three-dimensional image of a plurality of two-dimensional transverse cross-sectional images generated by the ultrasound device 2. By interacting with the computer 3, the physician 5 is able to delimit the unwanted tissue area or internal structure and direct the laser firing only to that delimited area. Additionally, those skilled in the art will understand and appreciate that a manual control system 4, is desirable, to permit the physician 5 to bypass the computer 3 and interact directly with the ultrasound device 2 and the laser 1.

The protruding distal end of each of the plurality of optical fibers 14 is configured to direct the laser irradiation at a pre-determined angle from the longitudinal axis of the catheter tube 12. According to the preferred embodiment of the present invention, though not to be construed as limiting the scope of the invention, each of the plurality of optical fibers 14 are configured to fire the laser irradiation at an angle of approximately 90° relative to the longitudinal axis of the optical fiber carrying the laser.

The firing of each of the plurality of optical fibers 14 is under the control of the computer system 3 and responds only to the delimiting input of the physician 5. As the plurality of optical fibers 14 are provided about the entire inner or outer circumference of the catheter 12 and each of the plurality of optical fibers 14 direct the laser firing generally perpendicular to the longitudinal axis of each optical fiber, the ultrasound laser catheter apparatus 10, of the present invention, is able to selectively irradiate virtually any sector of the 360° cross-sectional area about the catheter tube 12. It will be understood by those skilled in the art, therefore, that each of the plurality of optical fibers 14 fires only to a predetermined sector of the ultrasound image generated by the ultrasound device 2.

According to one preferred embodiment of the present invention, as illustrated with reference to FIGS. 2 and 4, the distal end 15 of each of the plurality of optical fibers is angularly sloped. With particular reference to FIG. 4, there is shown one of the plurality of optical fibers 14, the incident laser irradiation 20 and the refracted laser irradiation 21 which is angularly displaced from the longitudinal axis of the optical fiber 14. The angularly sloped distal end 15 of the optical fiber 14 refracts the incident laser irradiation 20. The refraction angle is determined by determining incidence angle $\alpha$ and the refraction angle $\beta$, with reference to a line/perpendicular to the slope of the distal end 15 of the optical fiber 14. The mathematical relation which exists between the incidence angle $\alpha$ and the refraction angle $\beta$ is the law of refraction: $\sin \alpha / \sin \beta = n$, where n is the index of refraction of the material used to form the optical fiber 14.

Accordingly, by varying the slope of the distal end 15 of optical fiber 14, the refraction angle of the refracted irradiation may be altered to a selected angle between about 0° and 90° as desired. Those skilled in the art will understand and appreciate that when employed in the above-described manner, different laser firing configurations are within the scope of the ultrasound laser catheter apparatus 10 of the present invention.

As described in the Barken Patent, the physician 5 controls the laser device 1, the ultrasound device 2 and the computer system 3. Additionally, in accordance with the present invention, the physician 5 also controls the ultrasound laser catheter 12. The ultrasound laser catheter 12, under the physician's control, interacts directly with the patient and provides ultrasonic information from the ultrasonic transducer 16 to the ultrasound device 2. The computer 3 processes the ultrasonic information from the ultrasound device and provides an reconstructed ultrasound image on an associated monitor. The physician 5 is then able to interact directly with the computer through suitable means of entering information, e.g., light pen, mouse, joy stick, digitizing tablet, keyboard entry, etc, to delimit the area of the displayed ultrasound image containing the unwanted internal tissue or structure. Based upon this entered information concerning the delimited tissue area, the computer system 3 instructs the laser device 1 to activate only those optical fibers 14 which are directed to fire at the sectors delimited on the ultrasound image. The computer also controls the intensity and duration of firing of each of the optical fibers 14.

Continuous ultrasound imaging of the internal tissue region permits the physician 5 to monitor and control the position of the ultrasound laser catheter 12 relative to the unwanted tissue to ensure complete destruction of the unwanted tissue or structure.

While the described ultrasound laser catheter apparatus 10 is primarily adapted for use with any natural tubing system, e.g., transrectally, intravessically, intratracheally, intraesophageally, or intrathecally, it utility is not limited to body system subserved by a natural passageway. In cases where no natural passage exists, such as breast tissue, liver, brain or kidney, the ultrasound laser catheter 12 may be introduced through an introductory balloon catheter 50 in FIG. 5.

Referring to FIG. 5, the introductory balloon catheter consists of a catheter wall 52 defining an internal lumen 54, a one-way valve 56 disposed in the terminal end of the lumen 54, a balloon 58 provided at the terminal end of the catheter and an inflating channel 60 in the catheter wall communicating with the balloon 58. In operation, a fluid, such as sterilized water, is introduced into inflating channel 60 from an external source and is conducted through inflating channel 60 into balloon 58, thereby inflating balloon 58. A one-way fluid restriction valve 62 is preferably provided in inflating channel 60 to prevent the reverse flow of fluid from the balloon 58. Alternatively, the fluid may be introduced through appropriate fluid tubing, not shown, inserted within inflating channel 60.

Where no natural passageway exists, the introductory balloon catheter 50 is introduced into the tissue through another dilatation catheter (not shown), which has been previously inserted in the tissue in a manner similar to the known techniques for introducing a nephrotomy tube into the kidney. Specifically, this technique entails targeting the lesion inside the body by any known imaging modality, e.g., CT Scan, Magnetic Resonance Imaging, Fluoroscopy, Mammography or Ultrasound. Once the lesion is targeted, a needle is introduced through the tissue to provide a channel in the tissue for introduction of the dilatation catheter. Serial dilatation is then performed by introducing a series of increasingly larger diameter catheters over a guide wire inserted into the tissue. In this manner, therefore, the tissue is gradually dilated until a dilatation catheter of sufficient diameter to accommodate the introductory balloon catheter 50 is provided in the tissue.

In a particular preferred embodiment of the present invention, the introductory balloon catheter 50 is disposed in the body, either through a natural passageway or through the serial dilatation technique, and the ultrasound laser catheter 12 inserted into the introductory balloon catheter 50. Where higher resolution ultrasound images are required or desired, the balloon 58 may be filled with fluid to facilitate better ultrasonic imaging.

It will be understood by those skilled in the art that the introductory balloon catheter 50 has utility separate and distinct from that in connection with the ultrasound laser catheter 12. For example, the introductory balloon catheter 50 may be used for introduction of an ultrasound transducer, a laser probe, an optical scope or any other type of instrumentation which may require an introductory passageway into the body's internal tissue. However, where the ultrasound laser catheter 12 requires an introductory passageway into internal tissue not subserved by a natural passageway, the introductory balloon catheter 50 provides such access.

The foregoing description is included to illustrate the preferred embodiments of the invention and their operation and is not meant, nor intended, to limit its scope or content. Rather many variations within the spirit and scope of the invention will be apparent to those skilled in the art. For example, the substitution of a plurality of ultrasonic transducers for a single ultrasonic transducer may be made to provide radial imaging of the tissue imaging with respect to the catheter, changes in materials, or usage may be made and still fall within the scope of the described and claimed invention.

What is claimed is:

1. A catheter system for destroying unwanted internal tissue, comprising:
    catheter tubing having a central axis, proximal and distal ends and a lumen;
    a plurality of optical fibers disposed about a circumference of said catheter tubing, each of said plurality of optical fibers having proximal and distal ends thereof and extending along the length of said catheter tubing, each of said plurality of optical fibers further comprising means for directing laser irradiation, transmitted from the distal end of each of said plurality of optical fibers, away from said central axis of the catheter tubing;
    at least one ultrasound imaging means associated with said catheter tubing for applying ultrasonic signals to internal tissue and receiving and processing said applied ultrasonic signals to display an ultrasonic image of said internal tissue;
    laser irradiation means for generating and supplying laser irradiation to each of said plurality of optical fibers;
    interactive computer means for accepting input corresponding to an area and position of unwanted tissue from the ultrasonic image displayed by said at least one ultrasound imaging means, evaluating a positional relationship between the area of unwanted tissue and said plurality of optical fibers and identifying which of said plurality of optical fibers have an optical path corresponding to the position of the unwanted tissue;
    means for selecting only said identified plurality of optical fibers which have an optical path corresponding to the position of the unwanted tissue and which are to be fired; and
    control means operably coupled to said laser irradiation means for activating and controlling firing of said laser irradiation means to said selected plurality of optical fibers.

2. The catheter system for destroying unwanted internal tissue, according to claim 1, wherein said plurality of optical fibers is disposed about an inner circumference of said catheter tubing.

3. The catheter system for destroying unwanted internal tissue, according to claim 1, wherein said plurality of optical fibers is disposed about an outer circumference of said catheter tubing.

4. The catheter system for destroying unwanted internal tissue according to claim 1, wherein said lumen of said catheter tubing is closed.

5. The catheter system for destroying unwanted internal tissue, according to claim 1, wherein the distal end of each of said plurality of optical fibers protrudes beyond the distal end of said catheter tubing.

6. The catheter system for destroying unwanted internal tissue according to claim 1, wherein said means for directing laser irradiation further comprises an angled distal end of each of said plurality of optical fibers.

7. The catheter system for destroying unwanted internal tissue according to claim 1, wherein said ultrasound imaging means further comprises an ultrasound transducer for transmitting and receiving ultrasound signals and at least one pair of wires electrically connected to said ultrasound transducer extending the length of said catheter tubing.

8. An apparatus for destroying unwanted internal structures or tissue within a body, comprising:
    catheter tubing having proximal and distal ends and a lumen;
    a plurality of optical fibers disposed about a circumference of said catheter tubing, each of said plurality of optical fibers having a proximal and distal end thereof and extending along the length of said catheter tubing, wherein said distal end of each of said plurality of optical fibers protrudes beyond the distal end of said catheter tubing and has associated means for directing laser irradiation transmitted from the distal end of each of said plurality of optical fibers at a selected angle away from a central axis of the catheter tubing;
    at least one ultrasound imaging means associated with said catheter tubing for applying ultrasonic signals to internal tissue and receiving and processing said applied ultrasonic signals to display an ultrasonic image of said internal tissue;

laser irradiation means for generating and conducting laser irradiation to each of said plurality of optical fibers;

interactive computer means for accepting input corresponding to a positional relationship between said plurality of optical fibers and the unwanted internal tissue based upon information from said at least one ultrasound imaging means;

means for selecting only those optical fibers having an optical path corresponding to the positional relationship between said laser irradiation means and the unwanted internal tissue; and control means operably coupled to said laser irradiation means and to said ultrasound imaging means for controlling a firing of said laser irradiation means only to said selected plurality of optical fibers such that said laser irradiation is fired only at the unwanted tissue.

9. The apparatus according to claim 8, wherein said plurality of optical fibers is disposed about an inner circumference of said catheter tubing.

10. The apparatus according to claim 8, wherein said plurality of optical fibers is disposed about an outer circumference of said catheter tubing.

11. The apparatus according to claim 8, wherein said means for directing laser irradiation further comprises an angled distal end of each of said plurality of optical fibers.

12. The apparatus according to claim 8, wherein said ultrasound imaging means further comprises an ultrasound transducer for transmitting and receiving ultrasound signals and at least one pair of wires electrically connected to said ultrasound transducer extending the length of said catheter tubing.

13. The apparatus according to claim 8, wherein said apparatus further comprises introductory catheter means for introducing said catheter tubing, said plurality of optical fibers and said ultrasonic imaging means into an internal tissue area.

14. The apparatus according to claim 13, wherein said introductory catheter means further comprises:

flexible catheter tubing having proximal and distal ends and an internal lumen;

an inflatable balloon disposed at the distal end of said flexible catheter in communication with said internal lumen;

means for inflating said inflatable balloon, said means communicating with said balloon and said proximal end of said catheter tubing; and at least one one-way valve means disposed within said internal lumen for allowing entry into said balloon and preventing deflation of said balloon.

15. The apparatus according to claim 14, wherein said means for inflating said inflatable balloon further comprises an channel associated with said catheter tubing and gas tubing associated with said channel for conducting an inflating gas through said channel to said balloon.

16. A method for destroying unwanted tissue or structures within a body, comprising the steps of:

inserting, into an opening of a patient's body, a catheter comprising:

catheter tubing having a central axis and proximal and distal ends and a lumen;

a plurality of optical fibers for transmitting laser irradiation, said plurality of optical fibers being disposed about a circumference of said catheter tubing, each of said plurality of optical fibers having proximal and distal ends thereof and extending along the length of said catheter tubing, wherein each of said plurality of optical fibers further comprises means for directing laser irradiation, transmitted from the distal end of each of said plurality of optical fibers, away from said central axis of the catheter tubing; and at least one ultrasound imaging means associated with said catheter tubing for applying ultrasonic signals to internal tissue and receiving and processing said applied ultrasonic signals to display an ultrasonic image of said internal tissue;

activating said at least one ultrasound imaging means to transmit ultrasonic signals to internal tissue;

receiving ultrasonic echoes from said transmitted ultrasonic signals;

processing said received ultrasonic echoes with said ultrasound imaging means and displaying an ultrasound image of said internal tissue;

determining a positional relationship between the distal ends of said optical fibers and an area of unwanted tissue based upon the processed ultrasonic imaging echoes;

determining which of said plurality of optical fibers have a firing path corresponding to the determined positional relationship between the distal ends of said optical fibers and the area of unwanted tissue; and selecting and firing laser irradiation from only the determined plurality of optical fibers thereby directing said laser irradiation only to said area of unwanted tissue and having sufficient strength to destroy the unwanted tissue in said defined area.

17. The method in accordance with claim 16, wherein said method further comprising, prior to said step of inserting said catheter, the steps of:

inserting an introductory catheter comprising:

flexible catheter tubing having proximal and distal ends and an internal lumen;

an inflatable balloon disposed at the distal end of said flexible catheter in communication with said internal lumen;

means for inflating said inflatable balloon, said means communicating with said balloon and said proximal end of said catheter tubing; and at least one one-way valve means disposed within said internal lumen for allowing entry into said balloon and preventing deflation of said balloon; and inserting said catheter into said internal lumen of said introductory catheter such that the distal end of said catheter resides within said inflatable balloon of said introductory catheter.

18. The method in accordance with claim 16, wherein said step of firing laser irradiation further comprises firing said laser irradiation at a selected angle of from between about 0° to 90° away from said central axis of the catheter tubing.

* * * * *